(12) United States Patent
Suddaby

(10) Patent No.: US 10,470,895 B2
(45) Date of Patent: Nov. 12, 2019

(54) ENDOSCOPICALLY IMPLANTABLE FUSION IMPLANT FOR ENDOSCOPIC SPINAL SURGERY

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 86 days.

(21) Appl. No.: 15/678,801

(22) Filed: Aug. 16, 2017

(65) Prior Publication Data

US 2019/0053912 A1 Feb. 21, 2019

(51) Int. Cl.
*A61F 2/44* (2006.01)
*A61F 2/30* (2006.01)

(52) U.S. Cl.
CPC ...... *A61F 2/447* (2013.01); *A61F 2002/3052* (2013.01); *A61F 2002/30268* (2013.01); *A61F 2002/30271* (2013.01); *A61F 2002/30387* (2013.01); *A61F 2002/30405* (2013.01); *A61F 2002/30471* (2013.01); *A61F 2002/30492* (2013.01); *A61F 2002/30551* (2013.01); *A61F 2002/30556* (2013.01); *A61F 2002/30579* (2013.01); *A61F 2002/30601* (2013.01); *A61F 2002/30622* (2013.01); *A61F 2002/443* (2013.01)

(58) Field of Classification Search
CPC ...... A61F 2/4425; A61F 2/4455; A61F 2/447; A61F 2002/443
USPC ...................... 606/246–249; 623/17.11–17.16
See application file for complete search history.

(56) References Cited

U.S. PATENT DOCUMENTS

| | | | |
|---|---|---|---|
| 5,483,463 A | 1/1996 | Qin et al. | |
| 5,505,732 A | 4/1996 | Michelson | |
| 5,653,761 A | 8/1997 | Pisharodi | |
| 5,653,762 A | 8/1997 | Pisharodi | |
| 5,665,122 A | 9/1997 | Kambin | |
| 5,683,463 A | 11/1997 | Godefroy et al. | |
| 6,126,689 A * | 10/2000 | Brett | A61F 2/4455 623/17.15 |
| 6,174,334 B1 | 1/2001 | Suddaby | |
| 6,183,517 B1 | 2/2001 | Suddaby | |
| 6,332,895 B1 | 12/2001 | Suddaby | |

* cited by examiner

*Primary Examiner* — Julianna N Harvey
*Assistant Examiner* — Christina Negrellirodriguez
(74) *Attorney, Agent, or Firm* — Simpson & Simpson, PLLC

(57) ABSTRACT

An expandable intervertebral fusion implant, including an inferior component, including a first plurality of axial members and a first plurality of cross-members, a superior component, including a second plurality of axial members and a second plurality of cross-members, and at least one locking arm operatively arranged to lock the superior component at a distance from the inferior component.

21 Claims, 15 Drawing Sheets

ENDOSCOPICALLY IMPLANTABLE FUSION IMPLANT FOR ENDOSCOPIC SPINAL SURGERY

FIELD

The present disclosure relates to orthopedic surgery, and more particularly to an expandable and deployable intervertebral fusion implant capable of being paced within an intervertebral disc space and expanded in vertical and lateral dimensions.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

One common tool used in these spinal surgical procedures is an endoscope. A representative endoscope 30 is shown in FIG. 7A. Endoscopes are complex biomedical devices. The complexity results from the need for fiberoptic bundles and multiple long narrow channels to be contained within a tubular structure that is constrained by the limited dimensions of the body cavity opening. As shown in FIG. 7A, endoscope 30 broadly comprises light guide connector 31, light guide tube 32, control body 33, and insertion tube 34. As will be described infra, the inflatable abrading device of the embodiment is introduced into the disc space via insertion tube 34. As shown in FIG. 7B, surgeon 40 uses the endoscope both to observe and guide the procedure via monitor 41, and to introduce and manipulate surgical instruments and tools during surgery on patient 45.

The endoscope is only one element of the system. Other required elements are a light source, video processor, monitor and water bottle. For the purpose of describing an endoscope in this disclosure, we refer to videoscopes, which represent a newer technology in endoscope development as compared to fiberoptic endoscopes. In videoscopes, the "viewing" fibre bundle is replaced by a miniature charged coupled device (CCD) video camera chip that transmits signals via wires.

Videoscopes include three major sections: connector 31 (sometimes referred to as the "umbilical" section), control body 33 and insertion tube 34. Endoscopes require a watertight internal compartment integrated through all components for electrical wiring and controls, which protects them from exposure to patient secretions during use and facilitates the endoscope being submerged for cleaning and subsequent disinfection. Example embodiments are not intended to be limited to any particular type of endoscope.

Control body 33 provides connections for four systems: the electrical system, the light system, the air and water system, and the suction system. A cable with video signal, light control, and remote switching from the video processor is connected in the electrical system. A watertight cap is required for leak testing and reprocessing. The electrical connector is the only opening to the internal components. The connector is inserted into the light source and directs light via the fiberoptic bundle in the light guide to the distal end of the insertion tube. Air pressure is provided from a pump to the air pipe, and the water bottle is also connected here (there is no water channel or water connection for bronchoscopes). In some endoscope models, the separate air and water channels merge just prior to the distal end where they exit through a single channel. In other models, the air and water channels are totally separate and do not merge. The air and water channels are usually of one millimeter internal diameter, which is too small for brushing. A portable or wall suction system is connected to the suction port. The Universal cord encases the electrical wiring and air, water and suction channels from the connector to the control section. Teflon® (PTFE) tubing is commonly used for channels, and advances in technology have led to more pliable and smooth materials for instrument channels with better anti-adhesion properties. The suction channel size can vary from two to four millimeters internal diameter depending on scope make and model. There is a biopsy port on the side of the insertion tube that allows instruments to be passed down the insertion tube to the distal end (referred to as the instrument channel or biopsy/suction channel).

Control body 33 has moveable knobs that allow the physician to control all scope functions. The angulation control knobs drive the angulation wires and control the bending section at the distal end of the insertion tube, thereby providing two-dimensional angulation. Locking mechanisms are provided to hold the bending section in a specific position. The suction cylinder and valve connects the suction channel to the instrument channel in the insertion tube. By pressing the valve button, suction can be provided to the instrument channel. The air/water cylinder and valve are similar to the suction cylinder/valve except that a two-way button valve is used in a dual channel cylinder thereby providing air or water to the lens at the distal end to wash and insufflate for better vision. Both valves are removable for cleaning. The air and water channels also require a cleaning adapter valve that is to be used at the end of each procedure. Insertion of the cleaning adapter initiates air flow through both air and water channels, and once activated, water is pumped through both channels. The instrument channel port (often referred to as the "biopsy port") is located on the lower part of the control section. It enters the instrument channel at a Y-piece union with the suction channel. A valve is required to close the port so that suctioning may be facilitated. Remote switches present on the top of the control section are usually programmable, allowing control of the video processor (i.e., contrast, iris and image capture functions).

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefited from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

U.S. Pat. No. 5,505,732 (Michelson), U.S. Pat. No. 5,653,761 (Pisharodi I), U.S. Pat. No. 5,665,122 (Kambin), and U.S. Pat. No. 5,683,463 (Godefroy et al.) disclose different prior art spinal implants. The implant disclosed in U.S. Pat. No. 5,483,463 (Qin et al.) is hollow and tubular, with communicating windows in the top and bottom surfaces. External ribs, which may be serrated, stabilize the implant once it is inserted between the vertebrae. Kambin discloses an intervertebral cage that is expandable by a wedging mechanism. The degree of expansion is rather limited. However, Michelson and U.S. Pat. No. 5,653,762 (Pisharodi II) disclose shaft-type tools used for installing implants. The prior art devices do not enable one to achieve great ranges of implant height.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

U.S. Pat. No. 6,174,334 (Suddaby I) and U.S. Pat. No. 6,332,895 (Suddaby II) disclose expandable cages using a ratcheting mechanism in the perimeter to achieve expansion.

While expandable interbody fusion devices are being increasingly employed in interbody fusion such that minimally invasive fusion techniques may be used, few have reached the capacity or capability of being deployed down the working channel of an endoscope or endoscopic access tube and therefore have not adequately achieved the ability to participate in true minimally invasive surgery.

SUMMARY

According to aspects illustrated herein, there is provided an expandable intervertebral fusion implant, comprising an inferior component, including a first plurality of axial members and a first plurality of cross-members, a superior component, including a second plurality of axial members and a second plurality of cross-members, and at least one locking arm operatively arranged to lock the superior component at a distance from the inferior component.

According to aspects illustrated herein, there is provided an expandable intervertebral fusion implant, comprising an inferior component, including a first axial member, a second axial member, a first cross-member connecting the first and second axial members, and a second cross-member connecting the first and second axial members, a superior component, including a third axial member, a fourth axial member, a third cross-member connecting the third and fourth axial members, and a fourth cross-member connecting the third and fourth axial members, a first locking arm connected to the third cross-member and arranged to engage the inferior component, and a second locking arm connected to the fourth cross-member and arranged to engage the inferior component.

According to aspects illustrated herein, there is provided an expandable and deployable interbody fusion implant capable of being placed in the intervertebral disc space with traditional minimally invasive techniques or endoscopically assisted means and expanded in situ in both a vertical and lateral dimension by virtue of internal arcuate arms which permit unidirectional vertical expansion and telescopic cross members which permit lateral expansion. Minimally invasive techniques may be employed so that adjacent intervertebral elements can be stabilized thereby facilitating arthrodesis and long term stability.

It is the object of this invention to provide for an expandable intervertebral fusion implant that is both easy to deploy and capable of being deployed through the barrel of an endoscope or through the working channel of a conduit employed for endoscopic spine access.

It is also intended that this device be capable of being utilized in all standard open or minimally invasive surgery (MIS) techniques presently known in the art.

To achieve these objectives, an interbody device is formulated around a rectangular base having telescopic cross members such that the base can be expanded and enlarged in a lateral dimension after being placed in situ.

The centrally placed telescopic cross member also serves as a fulcrum to which oppositely situated radial arms are pivotally attached, each pair of pivotally attached arms having a corresponding mirror pair on the other side of the implant.

While the proximal portion of the arms is pivotally attached to the central telescopic cross member, the distal end is pivotally and slideably attached to the axial members of the superior rectangular component in a tongue and groove fashion with the tongue portion of the distal radial arm consisting of a cylindrical side member to permit simultaneous pivoting in the groove as well as translation along the groove as the implant is expanded and the superior rectangular surface is moved away from the inferior rectangular surface.

While the radial arms are attached to a telescopic cross member situated in the rectangular base and pivotally connected to the superior rectangular surface in a tongue and groove manner, a second set of arcuate arms is connected pivotally to the four corners of the superior rectangular surface component. These arcuate arms have hooks or teeth that can engage a protrusion or a stop emanating from the floor of the inferior rectangular surface such that the arcuate arm can slide only unidirectionally unless it is physically maneuvered away from contact with the stop on the inferior surface.

In the unexpanded state, the arcuate arms lie in a roughly parallel fashion along the longitudinal axis of the superior and inferior rectangular surfaces, but as the two surfaces are separated away from each other by an expansion device, the arcuate arms slide along the stop, held in intimate juxtaposition by a leaf spring near the pivotal axis at the superior corner of the superior rectangular surface.

As expansion occurs, the arcuate arms are progressively advanced to a new hook or toothed position along the outer perimeter allowing unidirectional expansion in a ratchet like fashion. Disengagement can occur by partial expansion to the next position and folding the arcuate arms parallel to the axis utilizing the expansion device.

Alternately, if ideal expansion is achieved vertically the expansion device is collapsed leaving the arcuate arms engaged with the stop and firmly fixed at the chosen expanded level.

Lateral expansion of the device may be achieved by using the expansion device to affect a lateral directed force parallel to the telescopic cross members. The telescopic cross members also expand unidirectionally such that the optimal width of the implant can be achieved.

Once optimal height and width of the implant is achieved the expansion device is disengaged, the implant is then filled with fusion material and left in situ.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, and/or pneumatics.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1:
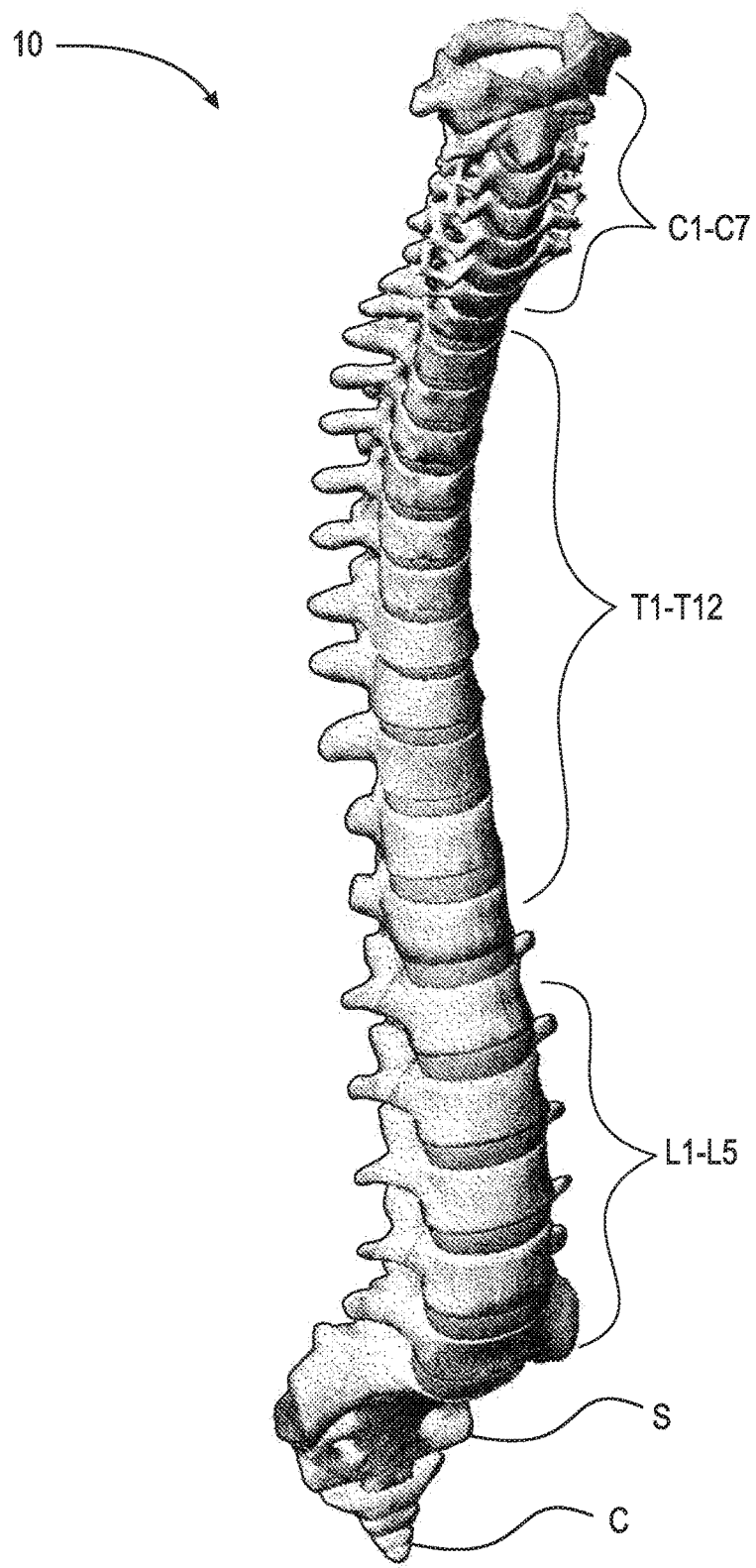
FIG. 1 is an anterior perspective view of a spinal column.
Figure 2:
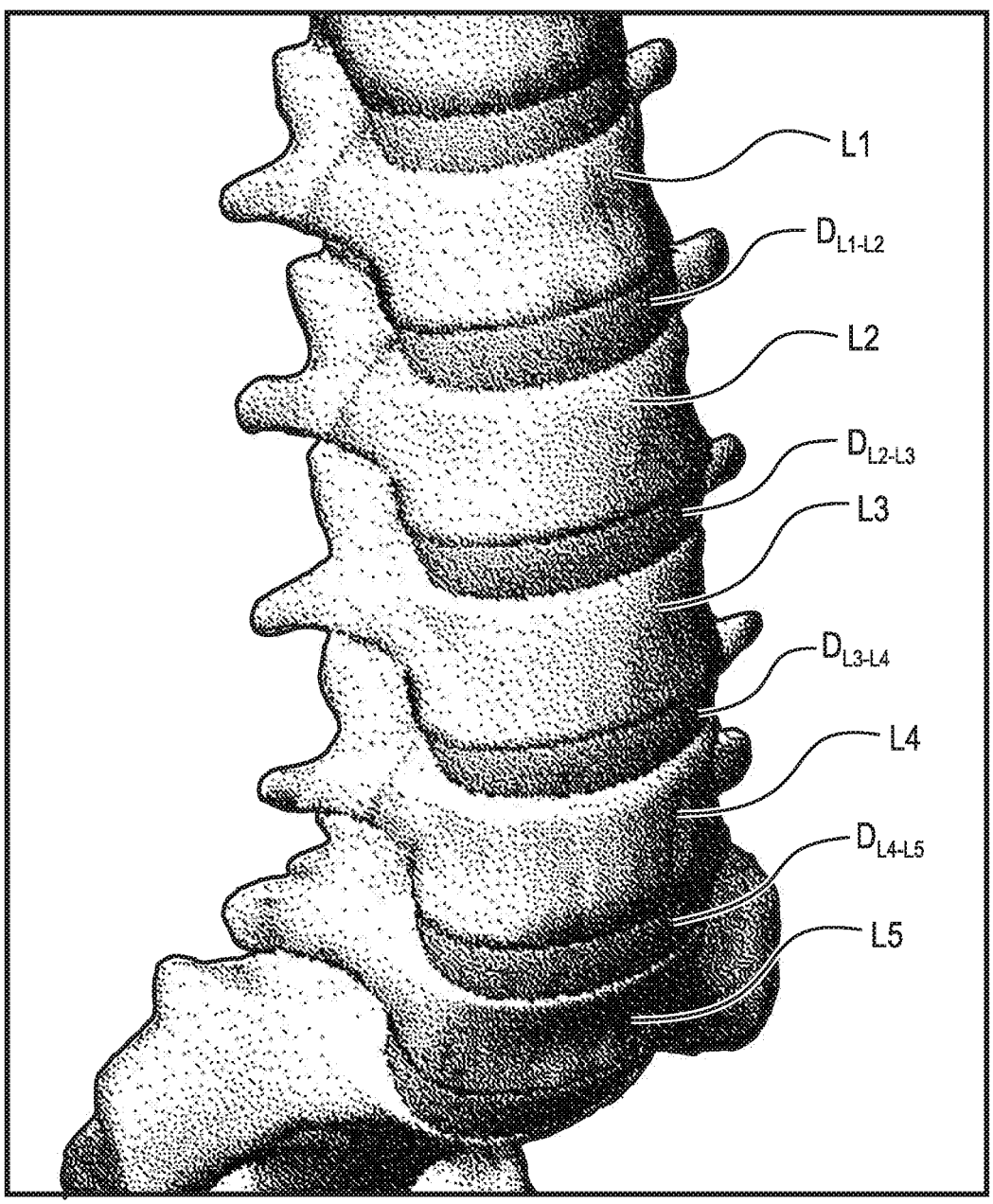
FIG. 2 is an anterior perspective view of the lumbar section of the spinal column shown in FIG. 1.
Figure 3:
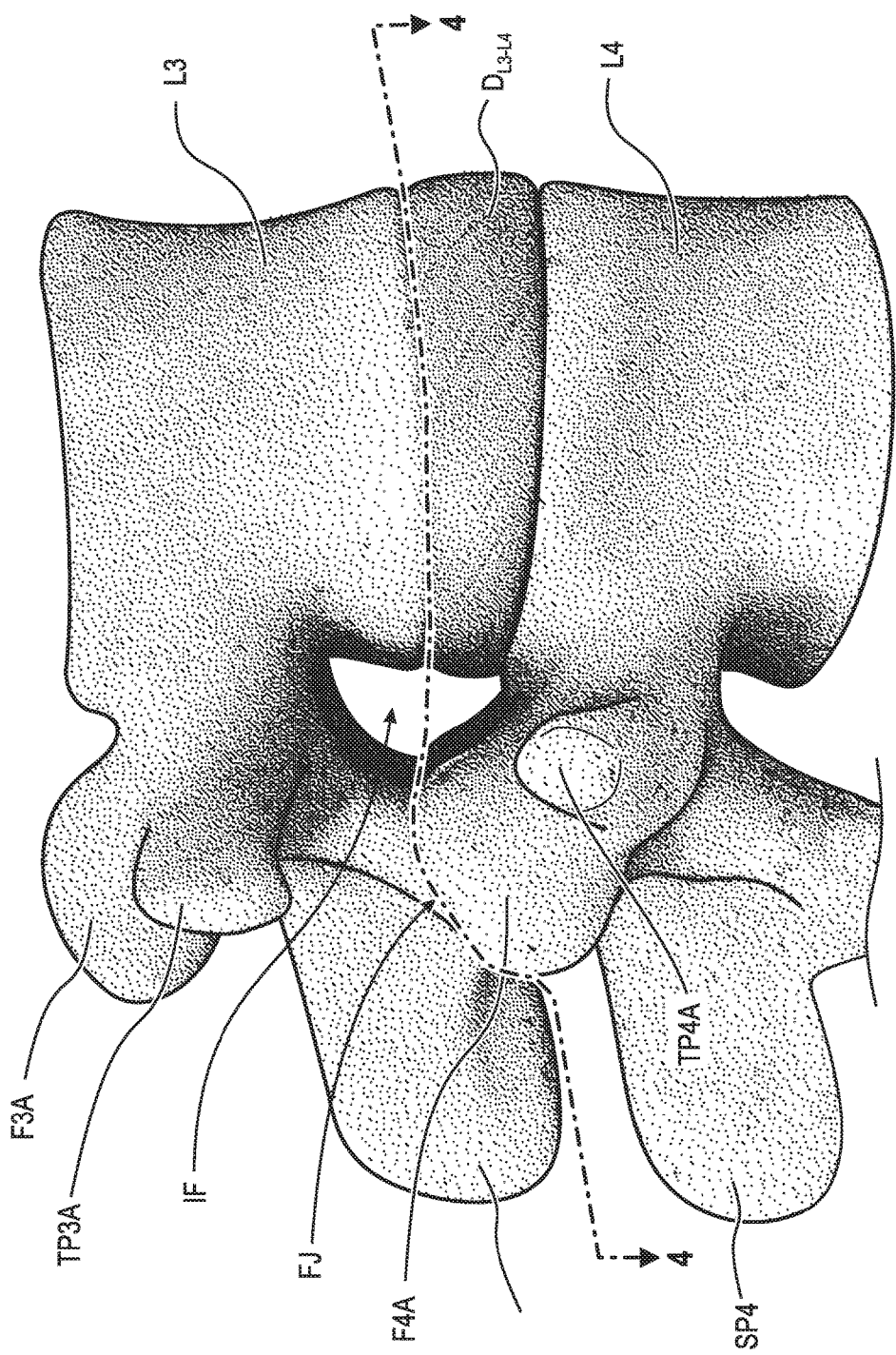
FIG. 3 is a lateral perspective view of two vertebrae, a disc, and related spinal anatomy.
Figure 4:
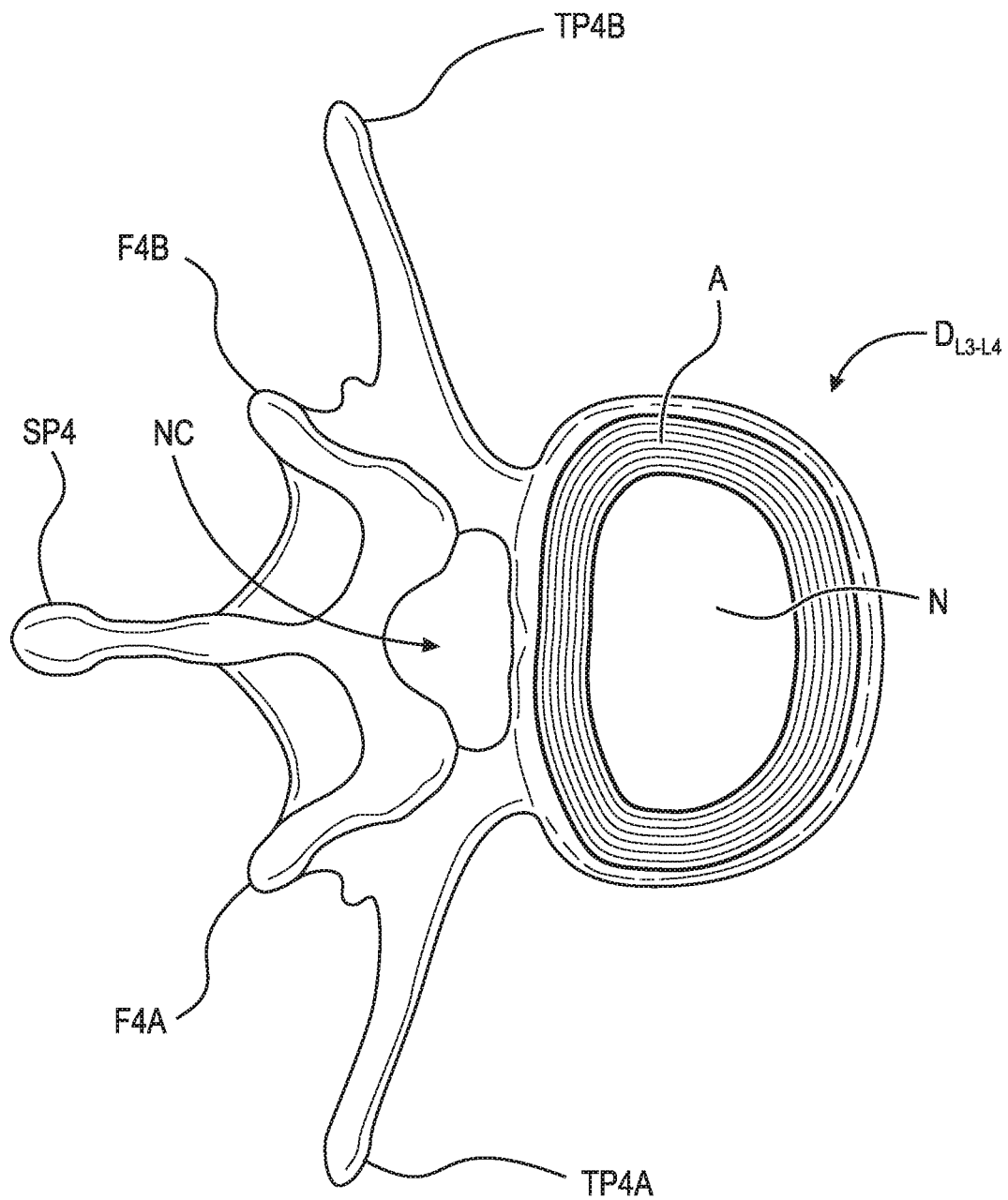
FIG. 4 is a top view of a section of the spinal column, taken generally along line 4-4 in FIG. 3.
Figure 5:
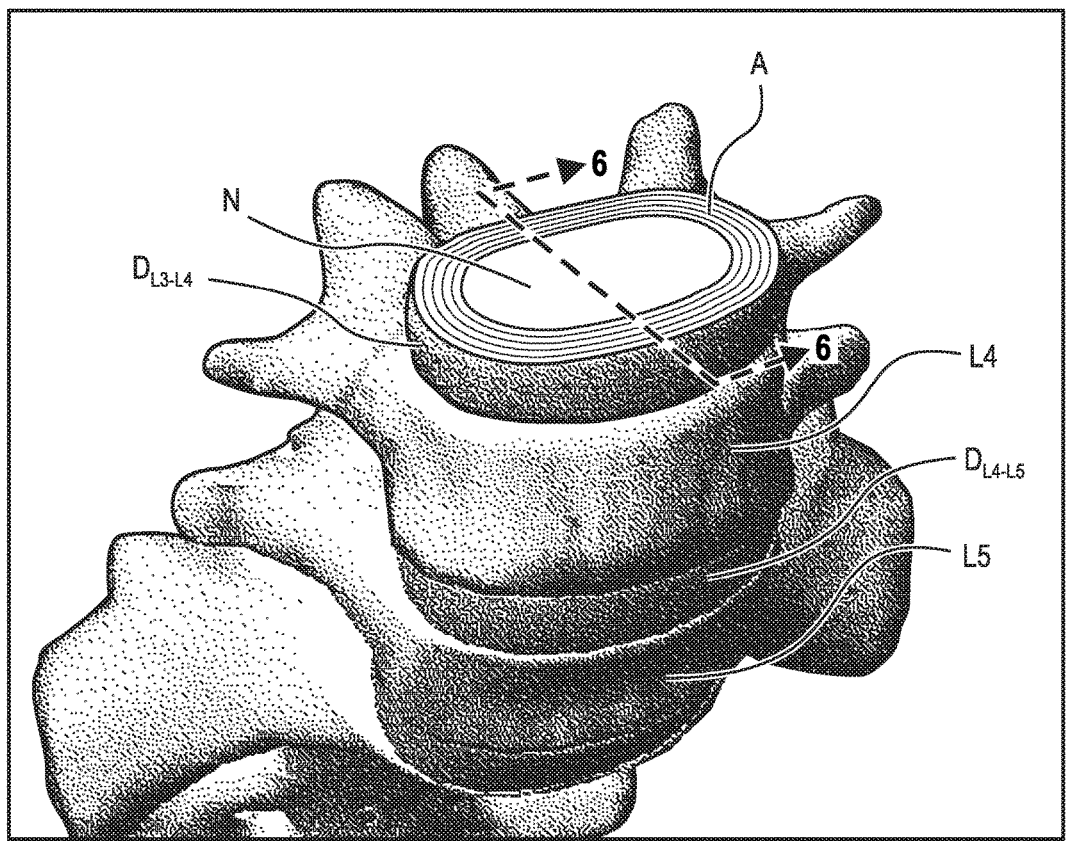
FIG. 5 is an enlarged anterior perspective view of the spinal column shown in FIG. 2, except with the top vertebra and all other structure above the top vertebra removed.
Figure 6:
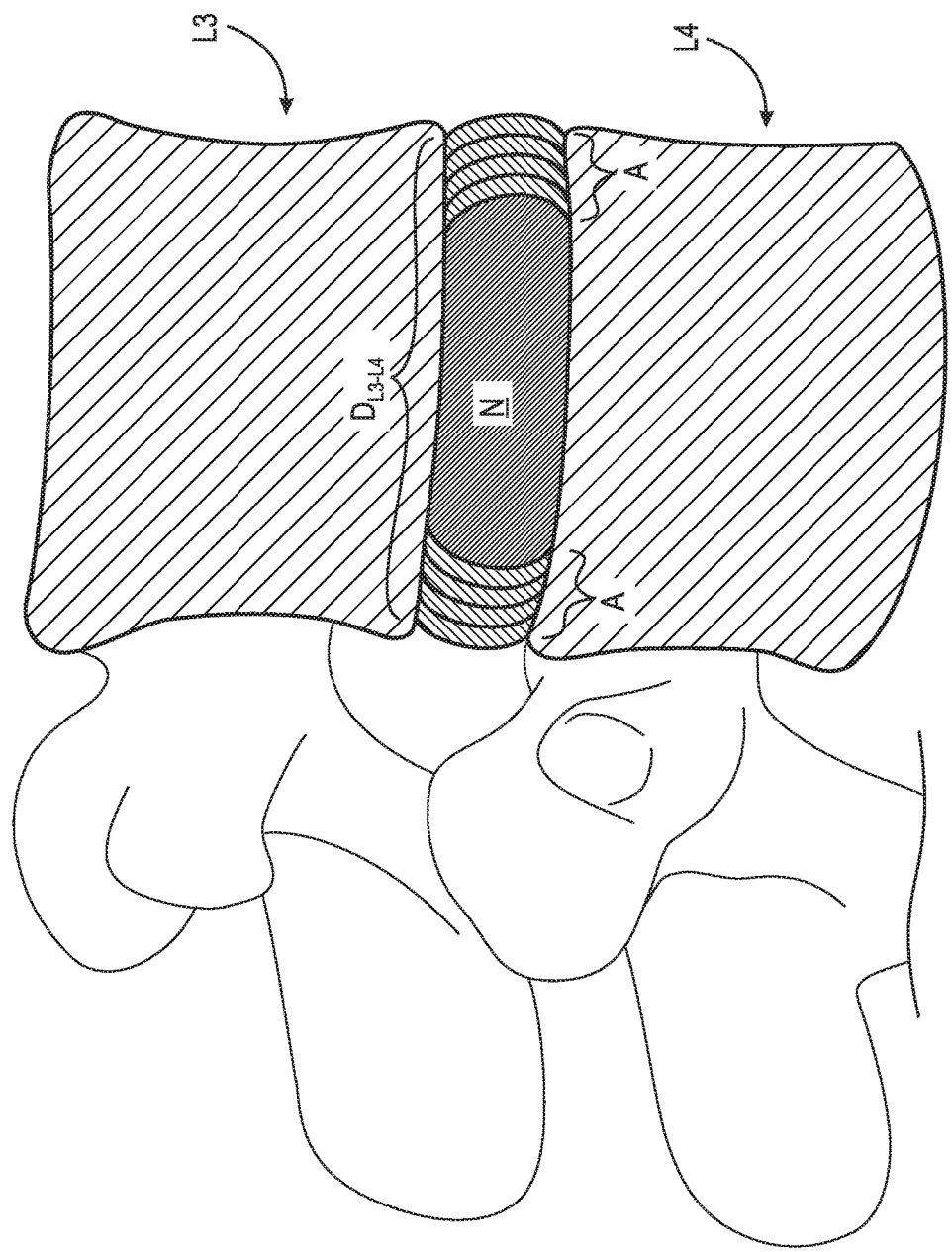
FIG. 6 is a partial cross-sectional view of the top and bottom vertebrae and disc, taken generally along line 6-6 in FIG. 5.
Figure 7:
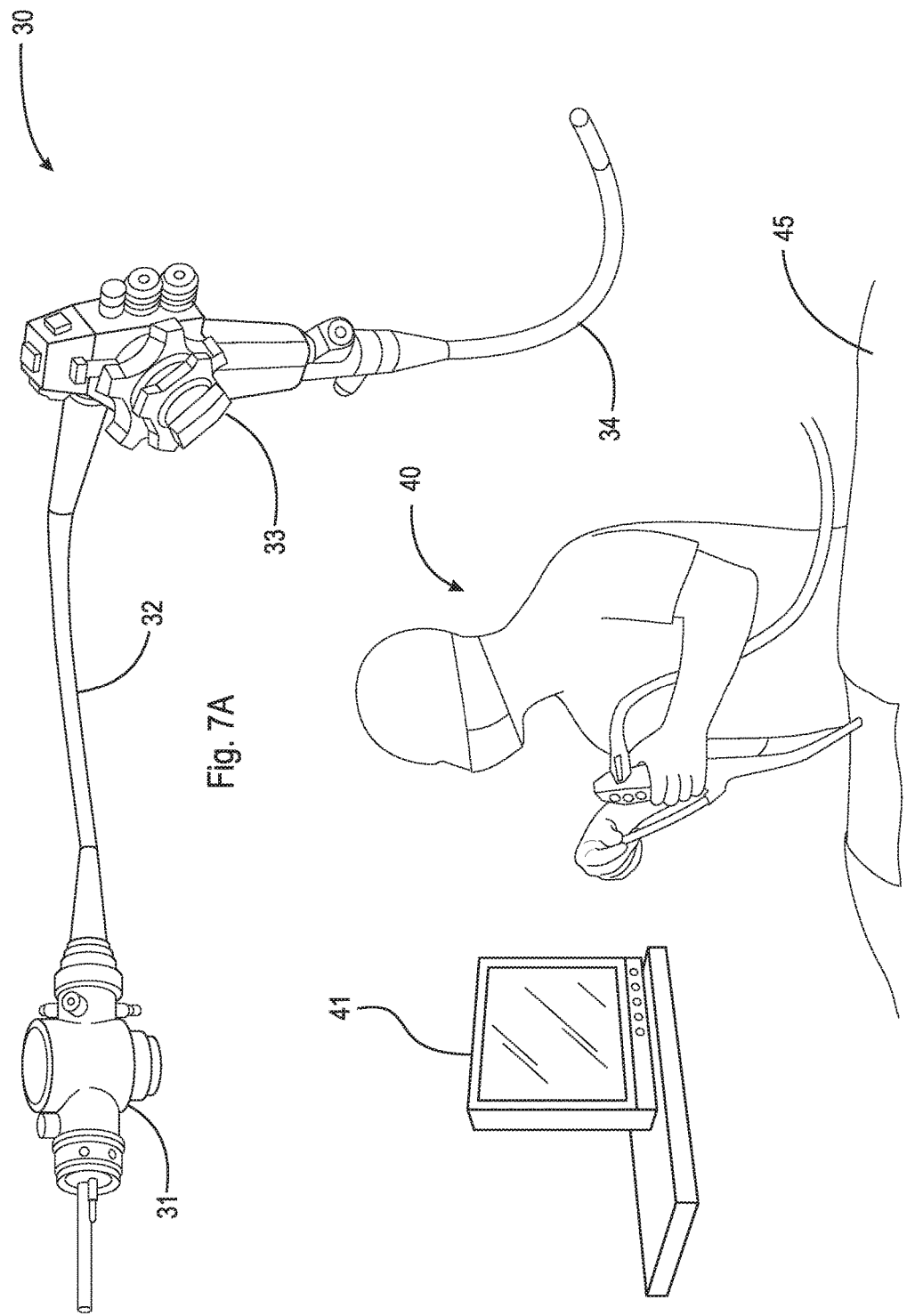
FIG. 7A is a view of a typical endoscope.
FIG. 7B illustrates use of the endoscope shown in FIG. 7A by a surgeon performing a discectomy (diskectomy)

Adverting now to the figures, and as described previously, FIGS. 1-6 depict various parts and sections of spinal anatomy, and FIGS. 7A and 7B depict a typical endoscope for use by a surgeon on a patient.

Figure 8:
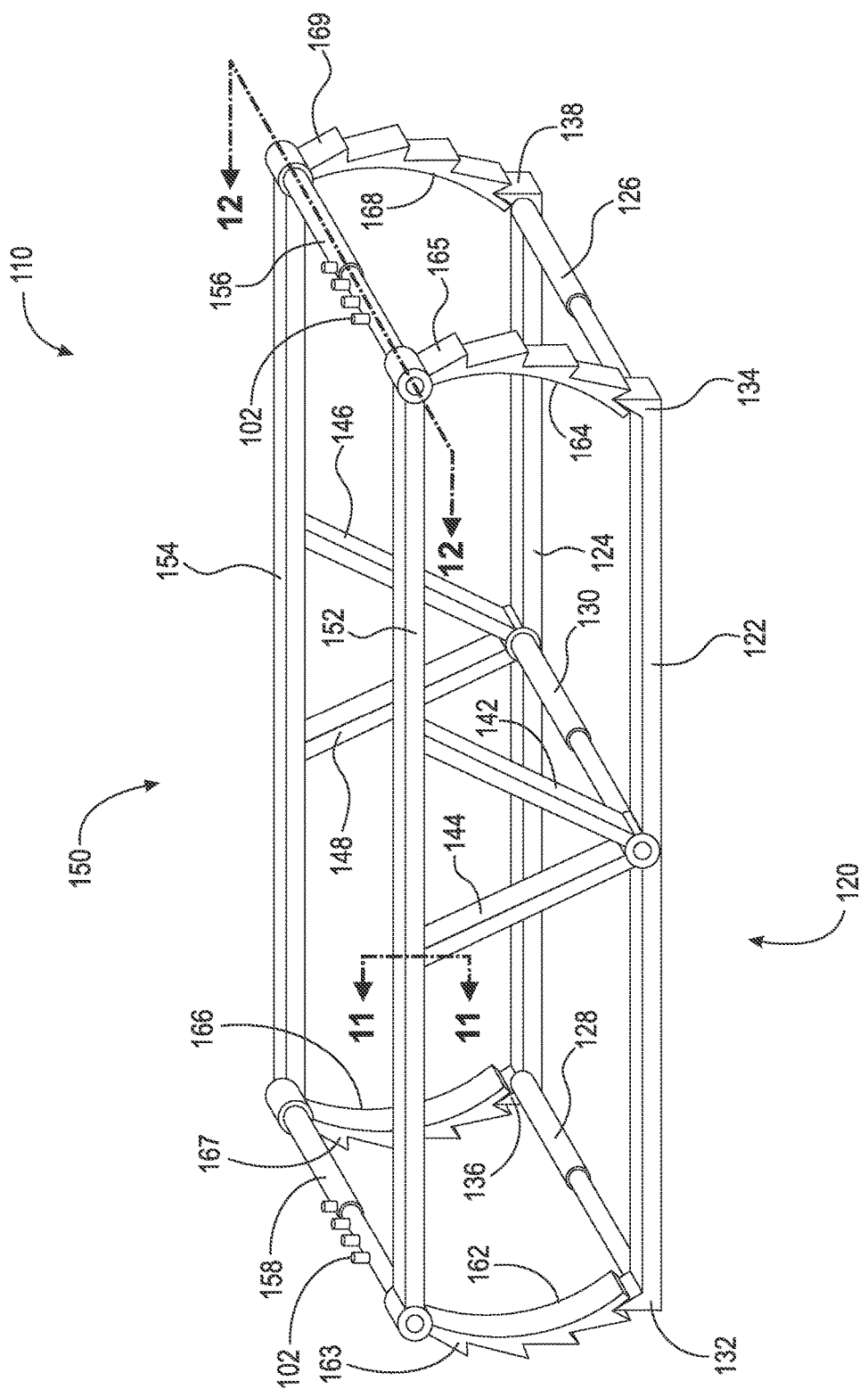
FIG. 8 is a top perspective view of an expandable intervertebral fusion implant, in an expanded state.
Figure 9:
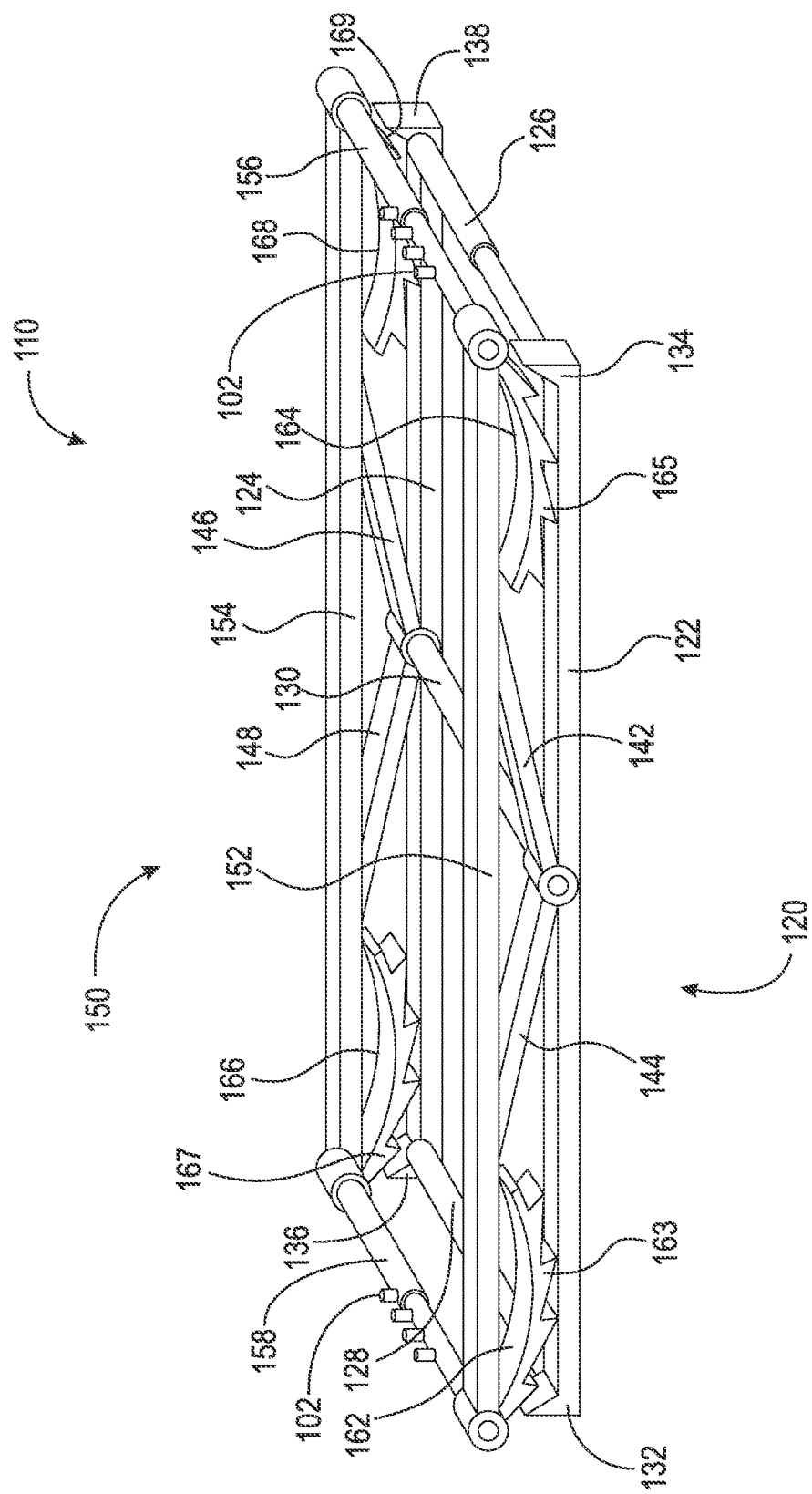
FIG. 9 is a top perspective view of the expandable intervertebral fusion implant shown in FIG. 8, in a collapsed state.

FIG. 8 is a top perspective view of expandable intervertebral fusion implant 110 in an expanded state. FIG. 9 is a top perspective view of expandable intervertebral fusion implant 110 shown in FIG. 8, in a collapsed state. Intervertebral fusion implant 110 generally comprises inferior component 120, superior component 150, support arms 142, 144, 146, and 148, and locking arms 162, 164, 166, and 168.

Inferior component 120 comprises axial members 122 and 124. Axial member 124 is connected to axial member 122 by telescopic cross-members 126, 128, and 130. Telescopic cross-members 126, 128, and 130 are adjustable such that expandable intervertebral fusion implant 110 is laterally expandable. For example, cross-members may comprise an inner rod slideable within an outer rod, as will be discussed in greater detail below. Cross-members 126 and 128 are fixed to respective ends of axial members 122 and 124. It should be appreciated that cross-members 126 and 128 do not have to be fixed at the ends of axial members 122 and 124, but rather can be fixed axially inward from the ends of axial members 122 and 124. Cross-member 130 is fixed to axial members 122 and 124 at their respective middles or substantially proximate thereto. In an example embodiment, axial members 122 and 124 are telescoping rods or beams. Axial member 122 comprises protrusions 132 and 134 extending therefrom. Protrusion 132 is located at or proximate a first end of axial member 122 and protrusion 134 is located at or proximate a second end of axial member 122. Axial member 124 comprises protrusions 136 and 138 extending therefrom. Protrusion 136 is located at or proximate a first end of axial member 124 and protrusion 138 is located at or proximate a second end of axial member 124. In an example embodiment, axial members 122 and 124 each comprise one or more protrusions located at various locations thereon. The one or more protrusions are operatively arranged on the axial members such that they engage the locking arms.

Superior component 150 comprises axial members 152 and 154. Axial member 154 is connected to axial member 152 by telescopic cross-members 156 and 158. Telescopic cross-members 126, 128, and 130 are adjustable such that expandable intervertebral fusion implant 110 is laterally expandable. For example, cross-members may comprise an inner rod slideable within an outer rod, as will be discussed in greater detail below. Cross-members 156 and 158 are fixed to respective ends of axial members 152 and 154. It should be appreciated that cross-members 156 and 158 do not have to be fixed at the ends of axial members 152 and 154, but rather can be fixed axially inward from the ends of axial members 152 and 154. In an example embodiment, axial members 152 and 154 are telescoping rods or beams.

Support arm 142 is pivotably connected at a first end to cross-member 130 at a proximate end of cross-member 130. Support arm 142 is slidingly and pivotably connected to axial member 152 at a second end, as will be discussed in greater detail below. Support arm 144 is pivotably connected at a first end to cross-member 130 at a proximate end of cross-member 130. Support arm 144 is slidingly and pivotably connected to axial member 152 at a second end, as will be discussed in greater detail below. Support arm 146 is pivotably connected at a first end to cross-member 130 at a distal end of cross-member 130. Support arm 146 is slidingly and pivotably connected to axial member 154 at a second end, as will be discussed in greater detail below. Support arm 148 is pivotably connected at a first end to cross-member 130 at a distal end of cross-member 130. Support arm 148 is slidingly and pivotably connected to axial member 154 at a second end, as will be discussed in greater detail below. Support arms 142, 144, 146, and 148 are arranged to provide axial and lateral support to expandable intervertebral fusion implant 110. As superior component 150 is separated from inferior component 120, support arms 142 and 144 and support arms 146 and 148 are moved toward each other at their respective second ends. As superior component 150 is moves closer to inferior component 120, support arms 142 and 144 and support arms 146 and 148 separate from each other at their respective second ends.

Locking arm 162 is pivotably connected at a first end to cross-member 158 at a proximate end of cross-member 158. Locking arm 162 comprises a plurality of teeth 163 extending therefrom. Teeth 163 are operatively arranged to engage with protrusion 132 such that, when superior component 150 is separated from inferior component 120, locking arm 162 falls against protrusion 132 and one of the plurality of teeth 163 is meshed with (i.e., catches on) protrusion 132. In an example embodiment, locking arm 162 is arcuate in shape with teeth 163 arranged on the radially outer circumferential surface. In an example embodiment, locking arm 162 is substantially linear.

Locking arm 164 is pivotably connected at a first end to cross-member 156 at a proximate end of cross-member 156. Locking arm 164 comprises a plurality of teeth 165 extending therefrom. Teeth 165 are operatively arranged to engage with protrusion 134 such that, when superior component 150 is separated from inferior component 120, locking arm 164 falls against protrusion 134 and one of the plurality of teeth 165 is meshed with (i.e., catches on) protrusion 134. In an example embodiment, locking arm 164 is arcuate in shape with teeth 165 arranged on the radially outer circumferential surface. In an example embodiment, locking arm 164 is substantially linear.

Locking arm 166 is pivotably connected at a first end to cross-member 158 at a distal end of cross-member 158. Locking arm 166 comprises a plurality of teeth 167 extending therefrom. Teeth 167 are operatively arranged to engage with protrusion 136 such that, when superior component 150 is separated from inferior component 120, locking arm 166 falls against protrusion 136 and one of the plurality of teeth 167 is meshed with (i.e., catches on) protrusion 136. In an example embodiment, locking arm 166 is arcuate in shape with teeth 167 arranged on the radially outer circumferential surface. The curvature of locking arm 166 may comprise a constant radius or a variable radius. The geometry of each of teeth 167 may be the same or may differ for one or more teeth. In an example embodiment, locking arm 166 is substantially linear.

Locking arm 168 is pivotably connected at a first end to cross-member 156 at a distal end of cross-member 156. Locking arm 168 comprises a plurality of teeth 169 extending therefrom. Teeth 169 are operatively arranged to engage with protrusion 138 such that, when superior component 150 is separated from inferior component 120, locking arm 168 falls against protrusion 138 and one of the plurality of teeth 169 is meshed with (i.e., catches on) protrusion 138. In an example embodiment, locking arm 168 is arcuate in shape with teeth 169 arranged on the radially outer circumferential surface. The curvature of locking arm 168 may comprise a constant radius or a variable radius. The geometry of each of teeth 169 may be the same or may differ for one or more teeth. In an example embodiment, locking arm 168 is substantially linear. Locking arms 162, 164, 166, and 168 may be biased into position by a leaf spring or similar spring as opposed to relying on gravity to fall into place.

Figure 10A:
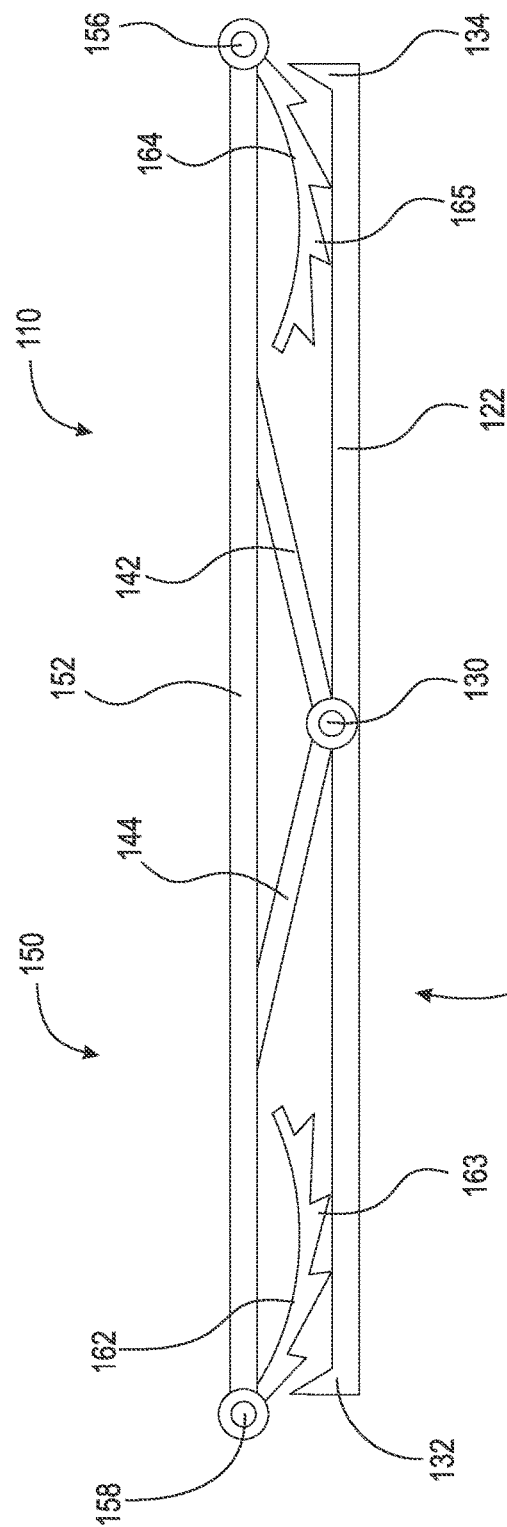
FIG. 10A is a front elevational view of the expandable intervertebral fusion implant shown in FIG. 9.

FIG. 10A is a front elevational view of expandable intervertebral fusion implant 110 in a fully collapsed state as shown in FIG. 9. As shown, in a fully collapsed state, none of teeth 163 or 165 are engaged with respective protrusions 132 and 134. Instead, locking arms 162 and 164 are approximately parallel with axial members 122 and 152. Similarly, support arms 142 and 144 are spread widely apart along axial member 152. Although not shown, the same is true on the distal side of expandable intervertebral fusion implant 110. None of teeth 167 or 169 are engaged with respective protrusions 136 and 138. Instead, locking arms 166 and 168 are approximately parallel with axial members 124 and 154. Similarly, support arms 146 and 148 are spread widely apart along axial member 154.

As superior component 150 is separated from inferior component 120 (i.e., vertical expansion), the arcuate shape of locking arms 162, 164, 166, and 168 cause them to extend radially outward, thus forcing respective teeth 163, 165, 167, and 169 into engagement with respective protrusions 132, 134, 136, and 138. To collapse expandable intervertebral fusion implant 110 after it has been expanded, locking arms 162, 164, 166, and 168 simply need to be forced back radially inward such that respective teeth 163, 165, 167, and 169 clear respective protrusions 132, 134, 136, and 138.

Figure 10B:
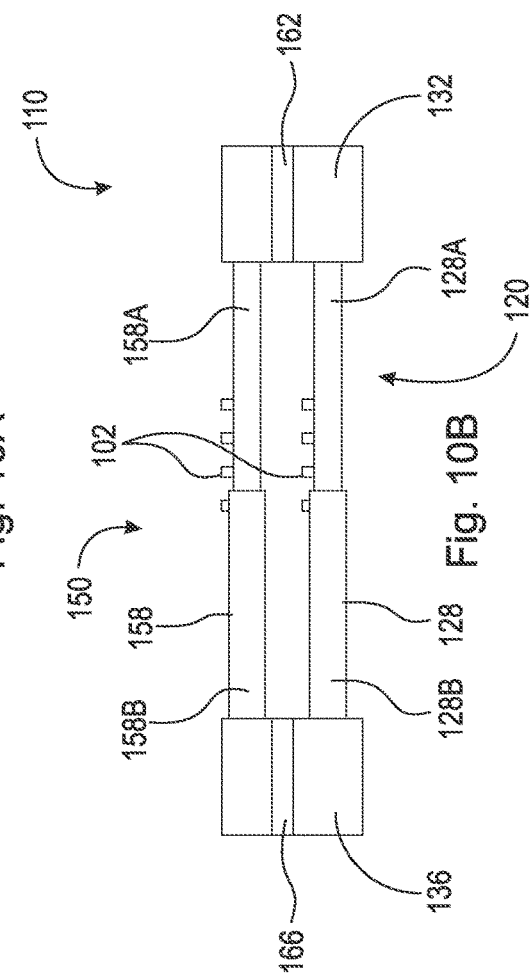
FIG. 10B is a side elevational view of the expandable intervertebral fusion implant shown in FIG. 9.

FIG. 10B is a side elevational view of expandable intervertebral fusion implant 110 in a fully collapsed state as shown in FIG. 9. Cross-members 158 and 128, along with cross-members 126, 130, and 156 (not shown in FIG. 10B) are telescoping such that expandable intervertebral fusion implant 110 is laterally expandable. Cross-member 158 comprises inner rod 158A arranged to slidingly engage outer rod 158B. Cross-member 158 may further comprise a plurality of pins 102 arranged to lock inner rod 158A and outer rod 158B at a set length. Pins 102 will be discussed in greater detail below. Cross-member 128 comprises inner rod 128A arranged to slidingly engage outer rod 128B. Cross-member 128 may further comprise a plurality of pins 102 arranged to lock inner rod 128A and outer rod 128B at a set length. Although not shown, cross-members 126, 130, and 156 are arranged substantially similar to cross-members 128 and 158. For example, cross-member 126 comprises inner rod 126A arranged to slidingly engage outer rod 126B, and may further comprise a plurality of pins 102 arranged to lock inner rod 126A and outer rod 126B at a set length. Cross-member 130 comprises inner rod 130A arranged to slidingly engage outer rod 130B, and may further comprise a plurality of pins 102 arranged to lock inner rod 130A and outer rod 130B at a set length.

Also shown in FIG. 10B are protrusions 136 and 132. Locking arm 166 rests on protrusion 136, however, none of teeth 167 are engaged with protrusion 136 as expandable intervertebral fusion implant 110 is in the fully collapsed state. Similarly, locking arm 162 rests on protrusion 132, however, none of teeth 163 are engaged with protrusion 132 as expandable intervertebral fusion implant 110 is in the fully collapsed state.

Figure 11:
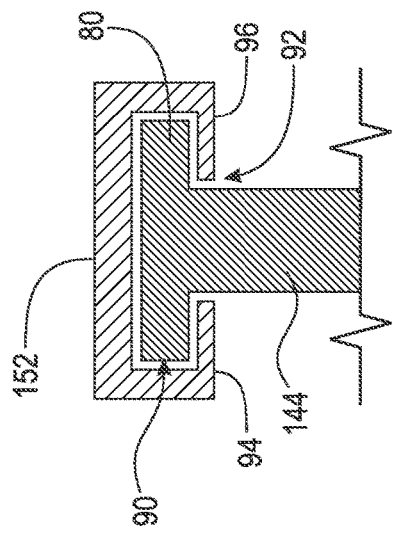
FIG. 11 is a cross-sectional view of a tongue and groove connection taken generally along line 12-12 in FIG. 8.

FIG. 11 is a cross-sectional view of a tongue and groove connection taken generally along line 11-11 in FIG. 8. Axial member 152 generally comprises channel 90, opening 92, and sides 94 and 96. Support arm 144 comprises runner 80 at one end and is pivotably connected to cross-member 130 at another end. Runner 80 may be pivotably connected to support arm 144 by, for example, a ball and socket type joint. Axial member 152 is designed to enclose runner 80 while still allowing support arm 144 to slidingly connect to axial member 152. Support arm 144 is arranged to engage axial member 152 such that support arm 144 can slide and at least partially pivot with respect to axial member 152 without disengaging from axial member 152. In an example embodiment, support arm 144 is at least partially rotatable with respect to axial member 152. An assembly of this type is known by those having ordinary skill in the art. In an example embodiment, support arm 144 is arranged to slide but not rotate with respect to axial member 152. It should be appreciated that support arm 142 is arranged substantially similar to support arm 144 with respect engagement with axial member 152. It should also be appreciated that support arms 146 and 148 are arranged substantially similar to support arms 142 and 144 with respect to engagement with axial member 154.

Figure 12:
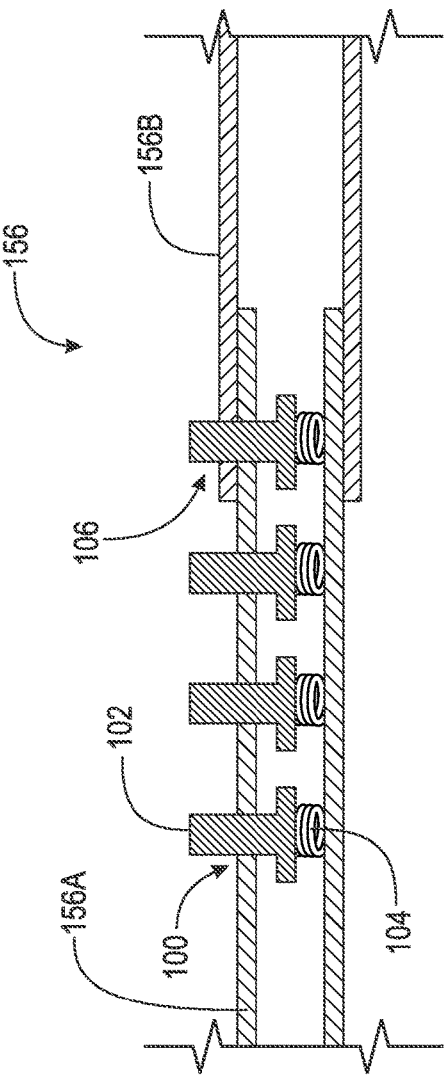
FIG. 12 is a cross-sectional view of a cross-member taken generally along line 12-12 in FIG. 8.

FIG. 12 is a cross-sectional view of cross-member 156 taken generally along line 12-12 in FIG. 8. As previously discussed, cross-member 156 comprises inner rod 156A arranged to slidingly engage outer rod 156B. In the embodiment shown, inner rod 156A comprises a plurality of pins 102 and corresponding spring members 104. Pins 102 protrude from holes 100 in inner rod 156A, specifically, pins 102 are forced radially outward through holes 100 by spring members 104. Pins 102 are forced radially inward such that inner rod 156A can be slid axially within outer rod 156B. One of pins 102 is aligned with hole 106 in outer rod 156B once the desired length of cross-member 156 is achieved. This similar locking mechanism (i.e., the push-pins) may be used on cross-members 126, 128, 130, and 158. In an example embodiment, inner rod 156A comprises radially outer threading and outer rod 156B comprises radially inner threading such that the length of cross-member 156 is adjustable by rotating one of inner rod 156A or outer rod 156B relative to the other. It should be appreciated that telescoping members are known in the art and that any suitable telescoping design may be used. In an example embodiment, one or more cross-members have a locking mechanism. In an example embodiment, no cross-members have a locking mechanism.

Figure 13A:
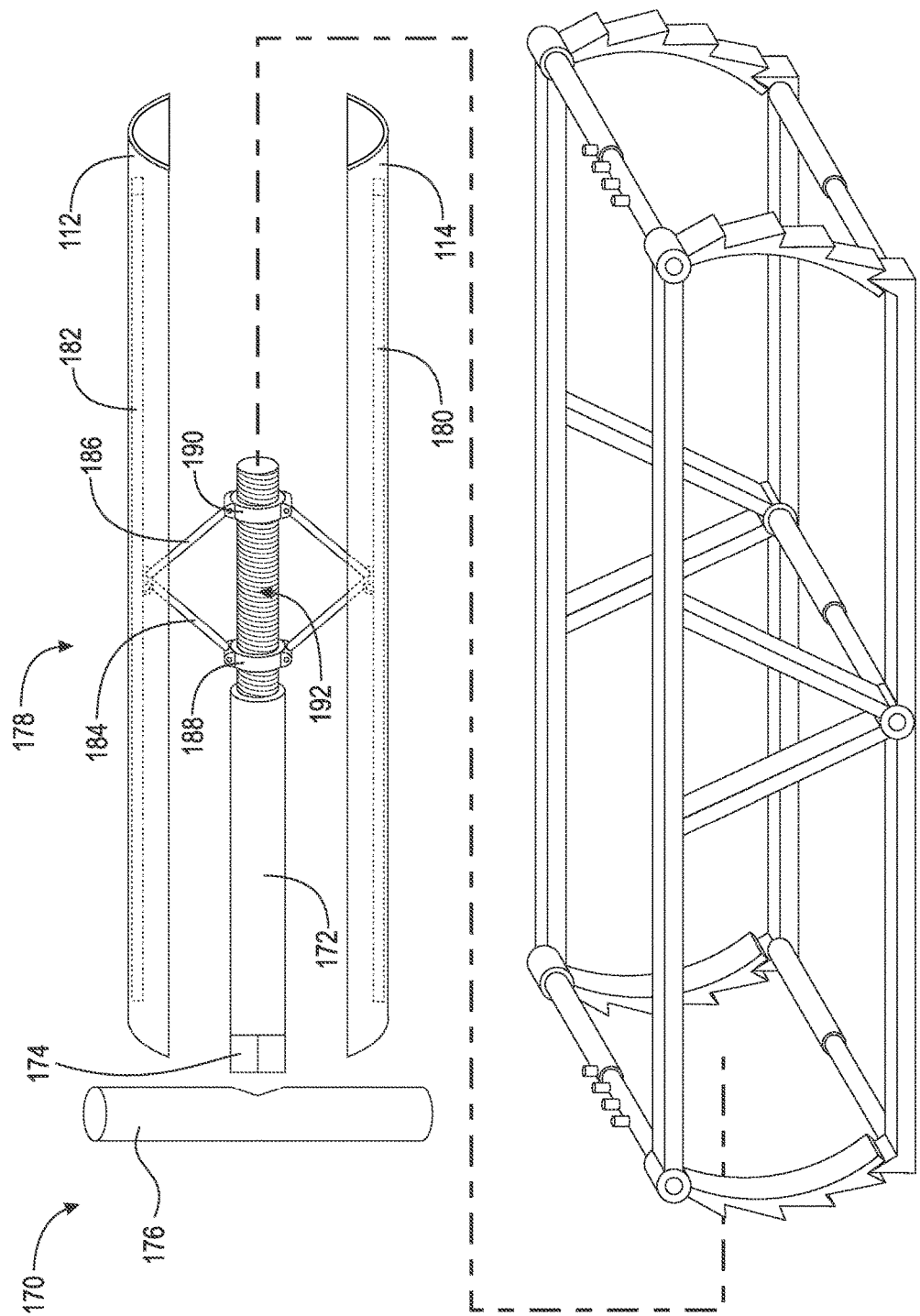
FIG. 13A is a perspective view of an expansion device arranged to expand an expandable intervertebral fusion implant.

FIG. 13A is a perspective view of expansion device 170 arranged to expand expandable intervertebral fusion implant 110. Expansion device 170 generally comprises shaft 172 including non-circular end 174 for receiving removable handle 176, and radially expandable structure 178. Radially expandable structure 178 generally comprises jaws 180 and 182, each of which is connected at its midpoint to the outer ends of pivoting arms 184 and 186, respectively. Jaws 180 and 182 may also be connected to semi-cylindrical shells 114 and 112, respectively. The inner ends of pivoting arms 184 and 186 are hinged to collars 188 and 190, respectively, or the like at the ends of screw thread 192 on shaft 172. The screw mechanism changes the spacing between collars 188 and 190 as handle 176 is rotated, thus driving jaws 180 and 182 in or out. Expansion device 170 is one example of a device that can be used to expand expandable intervertebral fusion implant 110. It should be appreciated however, that any suitable expansion device may be used.

Figure 13B:
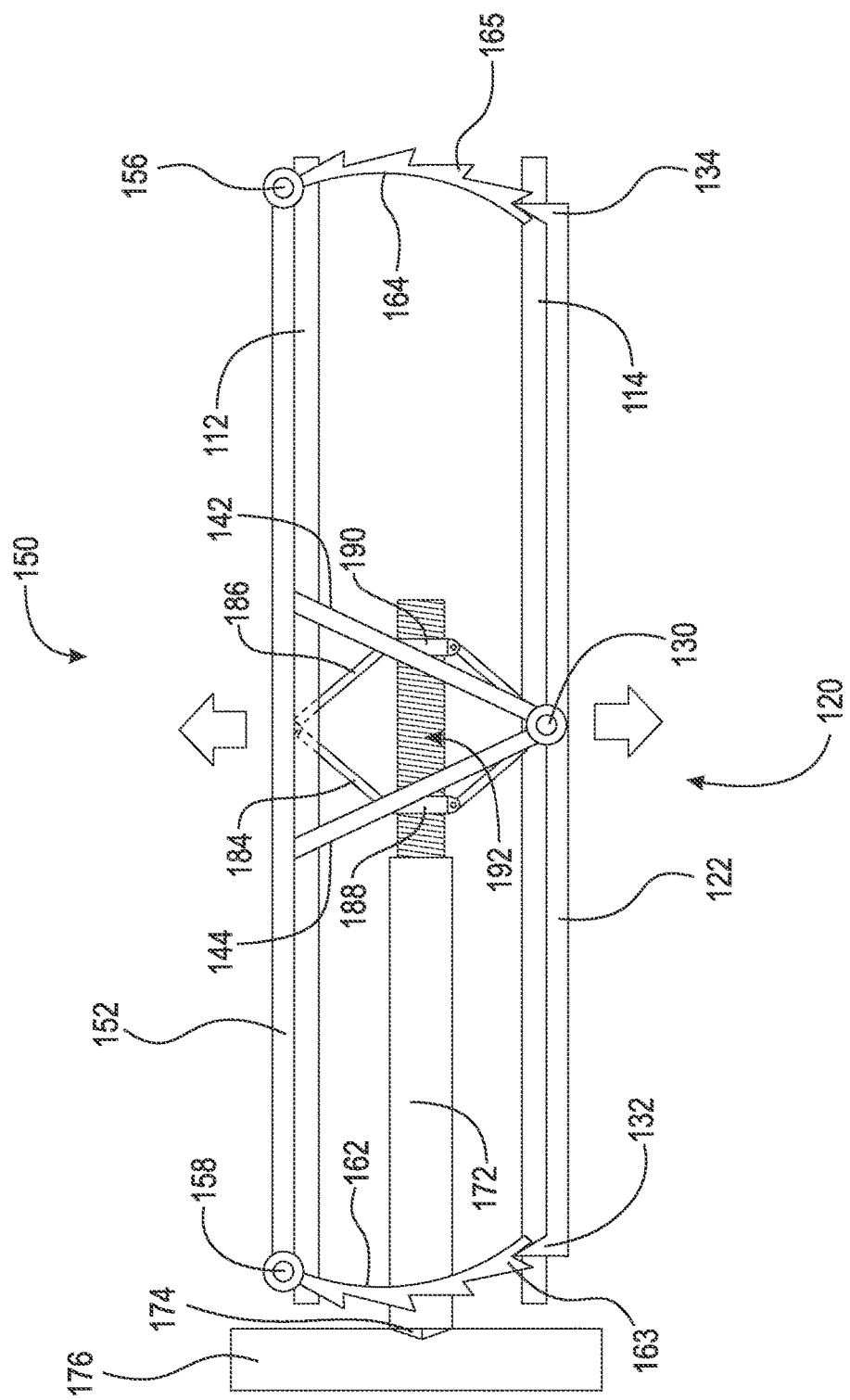
FIG. 13B is a front elevational view of the expansion device arranged in the expandable intervertebral fusion implant for expansion.

FIG. 13B is a front elevational view of expansion device 170 arranged in expandable intervertebral fusion implant 110 for expansion. To expand expandable intervertebral fusion implant 110, radially expandable structure 178 of expansion device 170 is inserted between inferior component 110 and superior component 150 from the side. With jaws 180 and 182 retracted, shell 112 abuts against cross-members 156 and 158 and shell 114 abuts against cross-members 126, 128, and 130. In an example embodiment, shell 114 abuts against cross-members 156 and 158 and shell 112 abuts against cross-members 126, 128, and 130. Then jaws 180 and 182 are spread by turning handle 176 clockwise, forcing shells 112 and 114 outward, and thus separating superior component 150 and inferior component 120. As superior component 150 is separated from inferior component 120, locking arms 162, 164, 166, and 168 fall into place and their corresponding teeth engage their corresponding protrusions, thus locking the superior component 150 at a set distance from inferior component 120. Once the desired distance (the optimal height) is reached, handle 176 is turned counter-clockwise to retract jaws 180 and 182. Once shells 114 and 112 disengage with respective cross-members, expansion device 170 may be removed from expandable intervertebral fusion implant 110. This same process may be used to expand expandable intervertebral fusion implant 110 laterally. For example, expansion device 170 would be rotated 90 degrees such that shell 112 abuts against support arms 142 and 144, and shell 114 abuts against support arms 146 and 148.

Figure 14:
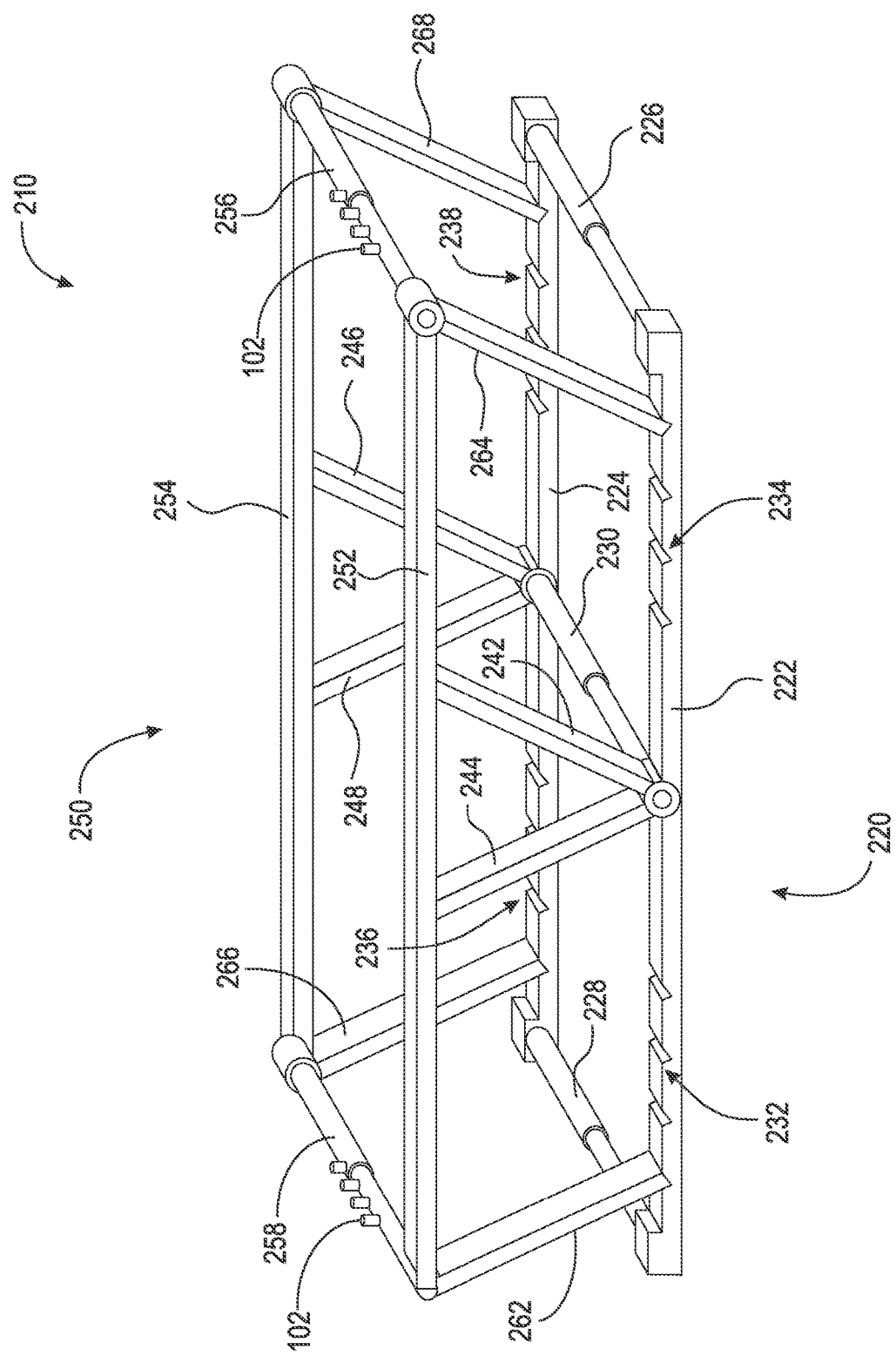
FIG. 14 is a top perspective view of an expandable intervertebral fusion implant; and, FIG. 15 is an anterior perspective view of a spinal column including the expandable intervertebral fusion implant shown in FIG. 8.

FIG. 14 is a top perspective view of expandable intervertebral fusion implant 210. Expandable intervertebral fusion implant 210 is substantially similar to expandable intervertebral fusion implant 110, albeit the locking mechanism. Intervertebral fusion implant 210 generally comprises inferior component 220, superior component 250, support arms 242, 244, 246, and 248, and locking arms 262, 264, 266, and 268.

Inferior component 220 comprises axial members 222 and 224. Axial member 224 is connected to axial member 222 by telescopic cross-members 226, 228, and 230. Telescopic cross-members 226, 228, and 230 are adjustable such that expandable intervertebral fusion implant 210 is laterally expandable. For example, cross-members may comprise an inner rod slideable within an outer rod, as was previously discussed. Cross-members 226 and 228 are fixed to respective ends of axial members 222 and 224. It should be appreciated that cross-members 226 and 228 do not have to be fixed at the ends of axial members 222 and 224, but rather can be fixed axially inward from the ends of axial members 222 and 224. Cross-member 230 is fixed to axial members 222 and 224 at their respective middles or substantially proximate thereto. In an example embodiment, axial members 222 and 224 are telescoping rods or beams. Axial member 222 comprises a plurality of slots 232 and 234. Slots 232 are located at or proximate a first end of axial member 222 and slots 234 are located at or proximate a second end of axial member 222. Axial member 224 comprises a plurality of slots 236 and 238. Slots 236 are located at or proximate a first end of axial member 224 and slots 238 are located at or proximate a second end of axial member 224.

Superior component 250 comprises axial members 252 and 254. Axial member 254 is connected to axial member 252 by telescopic cross-members 256 and 258. Telescopic cross-members 226, 228, and 230 are adjustable such that expandable intervertebral fusion implant 210 is laterally expandable. For example, cross-members may comprise an inner rod slideable within an outer rod, as was previously discussed. Cross-members 256 and 258 are fixed to respective ends of axial members 252 and 254. It should be appreciated that cross-members 256 and 258 do not have to be fixed at the ends of axial members 252 and 254, but rather can be fixed axially inward from the ends of axial members 252 and 254. In an example embodiment, axial members 252 and 254 are telescoping rods or beams.

Support arm 242 is pivotably connected at a first end to cross-member 230 at a proximate end of cross-member 230. Support arm 242 is slidingly and pivotably connected to axial member 252 at a second end as was previously discussed. Support arm 244 is pivotably connected at a first end to cross-member 230 at a proximate end of cross-member 230. Support arm 244 is slidingly and pivotably connected to axial member 252 at a second end as was previously discussed. Support arm 246 is pivotably connected at a first end to cross-member 230 at a distal end of cross-member 230. Support arm 246 is slidingly and pivotably connected to axial member 254 at a second end, as was previously discussed. Support arm 248 is pivotably connected at a first end to cross-member 230 at a distal end of cross-member 230. Support arm 248 is slidingly and pivotably connected to axial member 254 at a second end, as was previously discussed. Support arms 242, 244, 246, and 248 are arranged to provide axial and lateral support to expandable intervertebral fusion implant 210. As superior component 250 is separated from inferior component 220, support arms 242 and 244 and support arms 246 and 248 are moved toward each other at their respective second ends. As superior component 250 is moves closer to inferior component 220, support arms 242 and 244 and support arms 246 and 248 separate from each other at their respective second ends.

Locking arm 262 is pivotably connected at a first end to cross-member 258 at a proximate end of cross-member 258. Locking arm 262 is operatively arranged to engage one of slots 232 at a second end such that, when superior component 250 is separated from inferior component 220, locking arm 262 falls against slots 232 and the second end of locking arm 262 is meshed with (i.e., catches on) one of slots 232. In an example embodiment, locking arm 262 is arcuate in shape. In an example embodiment, locking arm 262 is substantially linear.

Locking arm 264 is pivotably connected at a first end to cross-member 256 at a proximate end of cross-member 256. Locking arm 264 is operatively arranged to engage one of slots 234 at a second end such that, when superior component 250 is separated from inferior component 220, locking arm 264 falls against slots 234 and the second end of locking arm 264 is meshed with (i.e., catches on) one of slots 234. In an example embodiment, locking arm 264 is arcuate in shape. In an example embodiment, locking arm 264 is substantially linear.

Locking arm 266 is pivotably connected at a first end to cross-member 258 at a distal end of cross-member 258. Locking arm 266 is operatively arranged to engage one of slots 236 at a second end such that, when superior component 250 is separated from inferior component 220, locking arm 266 falls against slots 236 and the second end of locking arm 266 is meshed with (i.e., catches on) one of slots 236. In an example embodiment, locking arm 266 is arcuate in shape. In an example embodiment, locking arm 266 is substantially linear.

Locking arm 268 is pivotably connected at a first end to cross-member 256 at a distal end of cross-member 256. Locking arm 268 is operatively arranged to engage one of slots 238 at a second end such that, when superior component 250 is separated from inferior component 220, locking arm 268 falls against slots 238 and the second end of locking arm 268 is meshed with (i.e., catches on) one of slots 238. In an example embodiment, locking arm 268 is arcuate in shape. In an example embodiment, locking arm 268 is substantially linear. Locking arms 262, 264, 266, and 268 may be biased into position by a leaf spring or similar spring as opposed to relying on gravity to fall into place.

Figure 15:
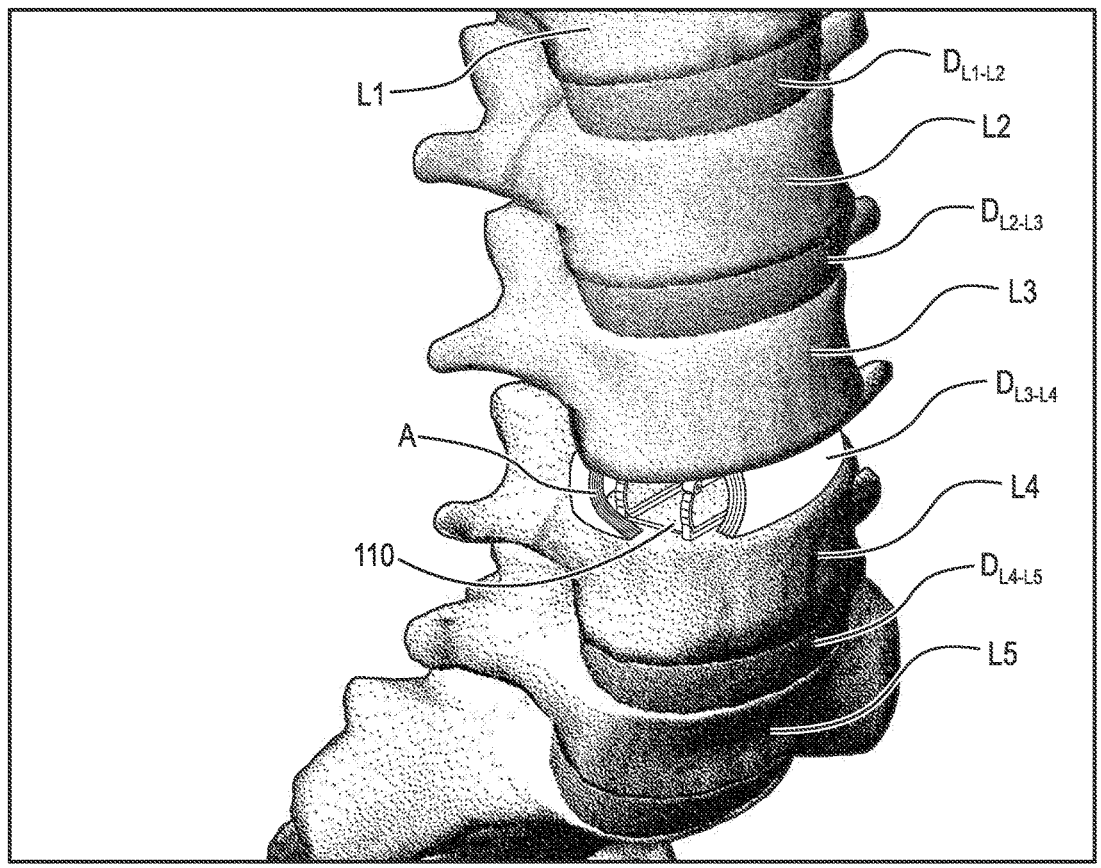

FIG. 15 is an anterior perspective view of a spinal column including expandable intervertebral fusion implant 110 shown in FIG. 8. Expandable intervertebral implant 110 is inserted into the spinal column between, for example, the L3 and L4 vertebrae, or where disc $D_{L3-L4}$ should be. Expandable intervertebral implant 110 is then vertically expanded until the desired height is reached. Expandable intervertebral implant 110 may be laterally expanded prior to insertion, or after insertion, as previously discussed. Expandable intervertebral implant 110 is then filled with fusion material and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
30 Endoscope
31 Light guide connector
32 Light guide tube
33 Control body
34 Insertion tube
40 Surgeon
41 Monitor
45 Patient
80 Runner
90 Channel
92 Opening
94 Side
96 Side
100 Holes
102 Pins
104 Spring members
106 Hole
110 Expandable intervertebral fusion implant
120 Inferior component
122 Axial member
124 Axial member
126 Cross-member
126A Inner rod
126B Outer rod
128 Cross-member
128A Inner rod
128B Outer rod
130 Cross-member
130A Inner rod
130B Outer rod
132 Protrusion
134 Protrusion
136 Protrusion 138 Protrusion
142 Support arm
144 Support arm
146 Support arm
148 Support arm
150 Superior component
152 Axial member
154 Axial member
156 Cross-member
156A Inner rod
156B Outer rod
158 Cross-member
158A Inner rod
158B Outer rod
162 Locking arm
163 Teeth
164 Locking arm
165 Teeth
166 Locking arm
167 Teeth
168 Locking arm
169 Teeth
170 Expansion device
172 Shaft
174 End
176 Removable handle
178 Radially expandable structure
180 Jaw
182 Jaw
184 Pivoting arm
186 Pivoting arm
188 Collar
190 Collar
192 Thread
210 Expandable intervertebral fusion implant
220 Inferior component
222 Axial member
224 Axial member
226 Cross-member
226A Inner rod
226B Outer rod
228 Cross-member
228A Inner rod
228B Outer rod
230 Cross-member
230A Inner rod
230B Outer rod
232 Slots
234 Slots
236 Slots
238 Slots
242 Support arm
244 Support arm
246 Support arm
248 Support arm
250 Superior component
252 Axial member
254 Axial member
256 Cross-member
256A Inner rod
256B Outer rod
258 Cross-member
258A Inner rod
258B Outer rod
262 Locking arm
264 Locking arm
266 Locking arm
268 Locking arm

What is claimed is:

1. An expandable intervertebral fusion implant, comprising:
   an inferior component, including:
      a first plurality of axial members; and,
      a first plurality of cross-members;
   a superior component, including;
      a second plurality of axial members; and,
      a second plurality of cross-members; and,
   at least one locking arm operatively arranged to, as the superior component is being displaced from the inferior component, slide longitudinally along the inferior component and lock the superior component at a vertical distance from the inferior component.

2. The expandable intervertebral fusion implant as recited in claim 1, wherein the at least one locking arm:
   is pivotably connected to the superior component; and,
   is arranged to engage at least one protrusion arranged on the inferior component.

3. The expandable intervertebral fusion implant as recited in claim 2, wherein the at least one locking arm comprises a plurality of teeth, wherein the plurality of teeth are arranged to engage the at least one protrusion.

4. The expandable intervertebral fusion implant as recited in claim 1, wherein the at least one locking arm:
   is pivotably connected to the superior component; and,
   is arranged to engage at least one slot arranged on the inferior component.

5. The expandable intervertebral fusion implant as recited in claim 1, further comprising at least one support arm, including:
   a first end pivotably connected to the inferior component; and,
   a second end slideably and pivotably connected to the superior component.

6. The expandable intervertebral fusion implant as recited in claim 5, wherein the second end comprises a runner, the runner slideably and pivotably engaging a channel in the superior component.

7. The expandable intervertebral fusion implant as recited in claim 1, wherein:
   in a fully collapsed state, the superior component is separated from the inferior component by a first distance; and,
   in a fully expanded state, the superior component is separated from the inferior component by a second distance, the second distance being greater than the first distance.

8. The expandable intervertebral fusion implant as recited in claim 1, wherein the first and second pluralities of cross-members are telescoping.

9. The expandable intervertebral fusion implant as recited in claim 8, wherein at least one cross-member of the first and second pluralities of cross-members comprises a plurality of locking pins operatively arranged to lock the at least one cross-member at a length.

10. The expandable intervertebral fusion implant as recited in claim 8, wherein at least one cross-member of the first and second pluralities of cross-members comprises:
    an outer rod comprising internal threads; and,
    an inner rod comprising external threads, the inner rod engaging the outer rod, wherein a length of the at least one cross-member is adjustable by rotating one of the inner rod or the outer rod relative to the other.

11. The expandable intervertebral fusion implant as recited in claim 1, wherein the superior component is separated from the inferior component using an expansion device.

12. An expandable intervertebral fusion implant, comprising:
   an inferior component, including:
      a first axial member;
      a second axial member;
      a first cross-member connecting the first and second axial members; and,
      a second cross-member connecting the first and second axial members;
   a superior component, including:
      a third axial member;
      a fourth axial member;
      a third cross-member connecting the third and fourth axial members; and,
      a fourth cross-member connecting the third and fourth axial members;
      a first locking arm connected to the third cross-member and arranged to engage the inferior component; and,
      a second locking arm connected to the fourth cross-member and arranged to engage the inferior component.

13. The expandable intervertebral fusion implant as recited in claim 12, wherein the first, second, third, and fourth cross-members are telescoping.

14. The expandable intervertebral fusion implant as recited in claim 13, further comprising at least one support arm, each of said at least one support arm including:
   a first end pivotably connected to the inferior component; and,
   a second end pivotably and slidingly connected to the superior component.

15. The expandable intervertebral fusion implant as recited in claim 14, wherein the first end is connected to a fifth cross-member, the fifth cross-member being telescoping and connecting the first and second axial members.

16. The expandable intervertebral fusion implant as recited in claim 14, wherein the second end is connected to the third or fourth axial members.

17. The expandable intervertebral fusion implant as recited in claim 13, wherein inferior component comprises a first protrusion and a second protrusion.

18. The expandable intervertebral fusion implant as recited in claim 17, wherein:
   the first locking arm comprises a first plurality of teeth operatively arranged to engage the first protrusion; and,
   the second locking arm comprises a second plurality of teeth operatively arranged to engage the second protrusion.

19. The expandable intervertebral fusion implant as recited in claim 13, wherein the inferior component comprises a first plurality of slots and a second plurality of slots.

20. The expandable intervertebral fusion implant as recited in claim 19, wherein:
   the first locking arm is operatively arranged to engage one of the first plurality of slots; and,
   the second locking arm is operatively arranged to engage one of the second plurality of slots.

21. An expandable intervertebral fusion implant, comprising:
   an inferior component, including:
      a first plurality of axial members; and,
      a first plurality of cross-members, each cross-member of the first plurality of cross-members being telescoping;
   a superior component, including;
      a second plurality of axial members; and,
      a second plurality of cross-members, each cross-member of the second plurality of cross-members being telescoping; and,
   at least one locking arm operatively arranged to lock the superior component at a distance from the inferior component.

* * * * *